US007282180B2

(12) United States Patent
Tibbe et al.

(10) Patent No.: US 7,282,180 B2
(45) Date of Patent: Oct. 16, 2007

(54) DEVICES AND METHODS TO IMAGE OBJECTS

(75) Inventors: Arjan Tibbe, Deventer (NL); Jan Greve, Oldenzaal (NL); Leon W. M. M. Terstappen, Huntingdon Valley, PA (US); Bart De Grooth, deceased, late of Oldenzaal (NL); by Jan Greve, legal representative, Enschede (NL)

(73) Assignee: Immunivest Corporation, Wilmington, DE (US)

( * ) Notice: Subject to any disclaimer, the term of this patent is extended or adjusted under 35 U.S.C. 154(b) by 452 days.

(21) Appl. No.: 10/612,144

(22) Filed: Jul. 2, 2003

(65) Prior Publication Data

US 2005/0003464 A1    Jan. 6, 2005

(51) Int. Cl.
*G01N 21/00* (2006.01)
(52) U.S. Cl. .................... 422/82.05; 435/34
(58) Field of Classification Search ............. 422/82.05; 382/133; 435/288.7, 34, 39, 40, 808
See application file for complete search history.

(56) References Cited

U.S. PATENT DOCUMENTS

| | | | |
|---|---|---|---|
| 5,340,749 A | 8/1994 | Fujiwara et al. | |
| 5,428,451 A | 6/1995 | Lea et al. | |
| 5,432,054 A | 7/1995 | Saunders et al. | |
| 5,876,593 A | 3/1999 | Liberti et al. | |
| 5,985,153 A | 11/1999 | Dolan et al. | |
| 6,151,405 A | 11/2000 | Douglass et al. | |
| 2004/0069857 A1* | 4/2004 | Leblans et al. | 235/494 |
| 2004/0252875 A1* | 12/2004 | Crandall et al. | 382/133 |
| 2005/0052646 A1* | 3/2005 | Wohlstadter et al. | 356/311 |

OTHER PUBLICATIONS

Racila, et al., "Detection and Characterization of Carcinoma Cells in the Blood," *Proc. Natl. Acad. Sci.*, 95: 4589-4594 (Apr. 1998).
A. Tibbe, B. Grooth, J. Greve, P. Liberti, G. Dolan and L. Terstappen, "Optical Tracking and Detection of Immunomagnetically Selected and Aligned Cells," *Nature Biotechnology*, 17: 1210-1213 (Dec. 1999).

* cited by examiner

*Primary Examiner*—Jill Warden
*Assistant Examiner*—Natalia Levkovich
(74) *Attorney, Agent, or Firm*—Joseph F. Aceto; James L. Wilcox

(57) ABSTRACT

Devices and methods for automated collection and image analysis are disclosed that enable identification or classification of microscopic objects aligned or deposited on surfaces. Such objects, e.g. detectably labeled rare target cells, are magnetically or non-magnetically immobilized and subjected to automated laser scanning to generate sequential digitized x-y sub-images or partial images of target and non-target objects that are combined to form reconstructed full images, thereby allowing detection, enumeration, differentiation and characterization of imaged objects on the basis of size, morphology and immunophenotype.

5 Claims, 8 Drawing Sheets

_US 7,282,180 B2_

DEVICES AND METHODS TO IMAGE OBJECTS

CROSS REFERENCE TO RELATED APPLICATIONS

This application claims priority under 35 U.S.C. section 119 (e) to U.S. Provisional Application Ser. No. 06/259,959, filed 5 Jan. 2001, the entire disclosure of which is incorporated by reference herein.

TECHNICAL FIELD

This invention relates generally to devices and methods to obtain to scan and obtain images of objects, and more particularly to images reconstructed from partial sub-images of object such as cells obtained from biological fluids that are distributed in a two-dimensional plane. The scanning and imaging technique provided by the invention is especially advantageous for the imaging of cells that are aligned by magnetic means and examined by digitized optoelectronic means.

BACKGROUND OF THE INVENTION

The invention of microscopy by Antoni van Leeuwenhoek in 1674 has enabled the visualization of microscopic entities such as cells. The introduction of dyes that stained different components of cells by Paul Ehrlich some two hundred years later in combination with light microscopy can be considered as the first step in the new era of cell analysis. Improvements in cell labeling technology and instrumentation that can identify and differentiate the differentially labeled cells have significantly improved our ability to explore the world of cell biology. In the last 25 years automated blood cell counters have replaced manual examination of cytochemically stained blood smears. Criteria used for cell classification by morphometric means involved parameters such as nuclear to cytoplasmic ratio, cell and nuclear size and shape, the number and size of cytoplasmic granules. As cells gradually change their morphological appearance during maturation, it introduces more uncertainty in substantial inter-observer variations in the assignation of the cells. Morphological changes associated with malignancies can be associated with cellular appearance during maturational processes and abnormal frequencies of atypical cells are often used as criteria for assigning such cells as malignant.

Improvements in cell classification have come from identification based on immunophenotype. Early techniques such as formation of rosettes of sheep erythrocytes around T-lymphocytes have been replaced by flow cytometric analysis of cells labeled with fluorescent antibodies recognizing specific cell surface or intracellular antigens. Multiparametric flow cytometry analysis has significantly improved the ability to enumerate and classify detected events on the basis of size and staining characteristics, but does not further discriminate detected events, for example, as cells by morphometric means. Present methods and devices using these principles are relied upon to diagnose and classify a variety of diseases such as leukemias and lymphomas, or to follow the progression of diseases such as AIDS. As technology improved, more information was obtained which in return lead to greater demands for expanding the sensitivity and specificity of detection methods for rare target species. An example of an application in need of further improvement is the identification and enumeration of circulating carcinoma cells of epithelial origin in the blood of cancer patients that may be present at frequencies of less than one carcinoma cell per ml of blood. Using a combination of epithelial cell enrichment by magnetic means in combination with analysis by multi-parametric flow cytometry, significant differences in the number of "circulating tumor cells" were found between healthy individuals and patients with breast cancer (Racila et al., Proc. Nat. Acad. Sci. 95, 4589-4594, 1998). In several studies, such "circulating tumor cells" (CTC) were defined as events expressing the following characteristics: positive for the epithelial cell marker cytokeratin, negative for the leukocyte marker CD45, positive staining with a nucleic acid dye, and light scattering properties that are compatible with cells. However, morphometric confirmations of the detected events as cells and further molecular evidence is lacking in flow cytometric methods, but is clearly needed to assure that the detected rare events are indeed tumor cells derived from a primary tumor. Automated image analysis systems have been introduced to reduce subjective errors in cell classification between different operators in manual methods, but such prior art systems without preliminary cell enrichment steps still inherently lack sensitivity. Several automated cell imaging systems have been described or are commercially available for cell analysis. The system developed by Chromavision, ACIS™ or Automated Cellular Imaging System (Douglass et al., U.S. Pat. No. 6,151,405) uses colorimetric pattern recognition by microscopic examination of prepared cells by size, shape, hue and staining intensity as observed by an automated computer controlled microscope and/or by visual examination by a health care professional. The system uses examination of cells on microscope slides and was designed for tissue sections. The SlideScan™ or MDS™ systems of Applied Imaging Corp. (Saunders et al., U.S. Pat. No. 5,432,054) is described as an automated, intelligent microscope and imaging system that detects cells or "objects" by color, intensity, size, pattern and shape followed by visual identification and classification. In contrast to the ACIS system this system has the ability to detect fluorescent labels which provides more capability. However, these and other currently available methodologies are not sufficiently sensitive for accurate classification and typing of rare events such as circulating tumor cells in blood. Accordingly, the present invention seeks to improve upon the aforementioned methodologies, and to provide simple and efficient means and methods for automated imaging of objects that can be used, for example, in conjunction with high sensitivity immunophenotyping, to permit detection, enumeration and accurate classification of rare target species, such as CTC in blood or other fluids.

SUMMARY OF THE INVENTION

This invention provides devices and methods that permit the application of novel imaging capabilities to such systems as the Cell Tracks™ cell analysis system as described by Tibbe et al. (Nature Biotech. 17, 1210-13, 1999). The devices and methods described by Tibbe and in the disclosure of this invention can also be applied to other target objects. However, the primary application is rapid immunomagnetic selection of rare cells from blood followed by automated alignment of the isolated cells and automated image analysis. Briefly, in a preferred embodiment of the invention, after magnetic collection and enrichment from blood, the magnetically labeled cells are aligned along ferromagnetic lines of nickel (Ni) and are scanned by a laser focused by means of a conventional objective lens such as from a compact disk player. Since the cells have been selectively stained with one or more fluorescent labels, the measured fluorescence emissions and the intensities can be used to identify or classify the cell type.

No liquid flow system is required by the system of the present invention. The magnetic fields induced by the angular magnets in proximity of the nickel lines keep the magnetically labeled cells in fixed positions. This allows revisiting the detected events after measuring the fluorescence emissions and intensities for a more extensive analysis to further identify the detected events. One can microscopically view the images of such events and apply independent morphometric criteria to identify the events as actual cells. Accordingly, in accordance with the present invention, the novel scanning and imaging method provides an improved diagnostic system for detection, classification and enumeration of cells, which comprises an efficient automated means for collecting and aligning imunomagnetically labeled target cells from body fluids, and in which such collected cells also bear at least one immuno-specific fluorescent label that differentiates target from non-target cells labeled with different fluorescent label(s). The images of the collected and aligned cells are reconstructed from individual digitized sub-images and their x-y coordinates, thereby providing full combined images of the objects and allowing improved classification of the detected objects as target events.

In accordance with the present invention, the new laser scanning and imaging techniques were integrated into a system such as the Cell Tracks system to obtain high quality fluorescence images. The discoveries described and claimed herein have greatly improved the detection, enumeration and classification of rare cells over systems and methods in prior art. Efficient detection of cells at very low frequencies, so called rare events, requires minimal sample handling to avoid losses of cells. Furthermore, the volume from which the rare cells are separated and enriched should be as large as possible to increase the sensitivity of detection. With the development and application of the disclosed novel techniques, fluorescent images of specific events can now be obtained resulting in a highly accurate identification, thus making the inventive system a powerful tool for the detection of rare events in body fluids.

Schematic representation of the Cell Tracks system which utilizes a preferred embodiment of the invention. The components important for imaging are shown in bold face.

Figure 2:
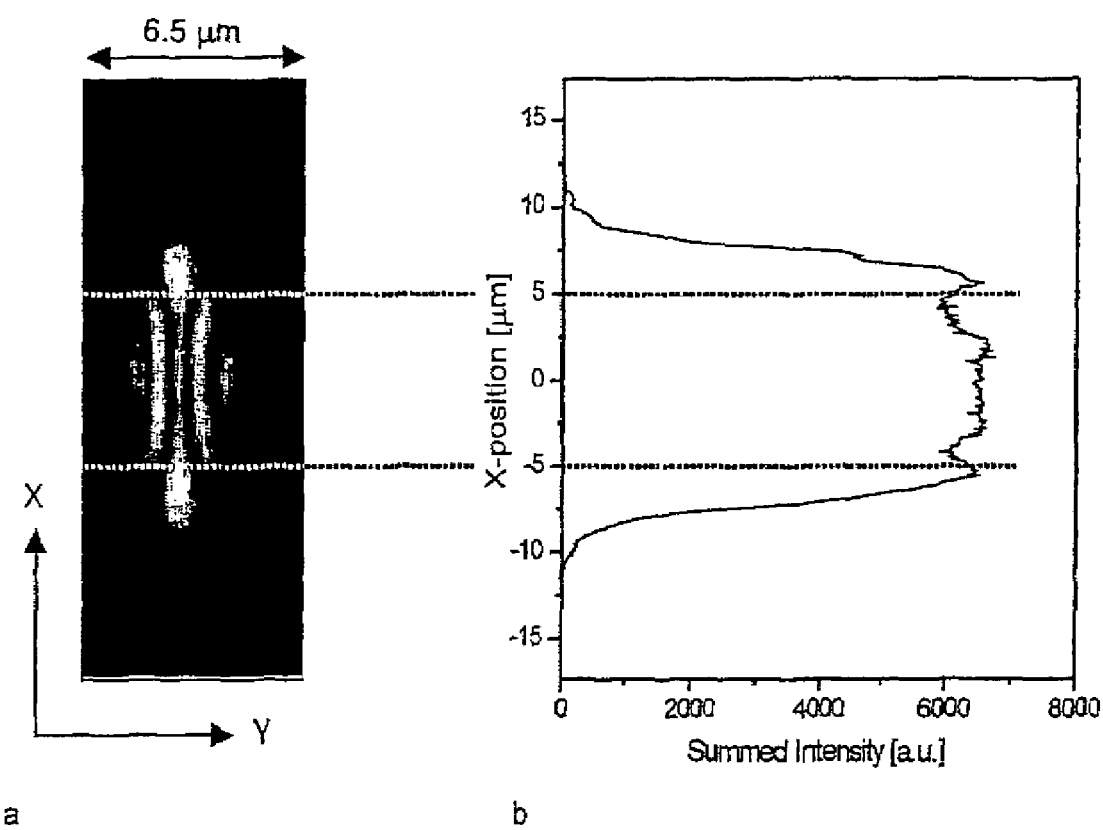

FIG. 2 a) Image of the illuminating focal spot as it is used for scanning the cells; short axis is 4 µm and long axis is 15 µm. The dotted lines indicate the position of the Ni lines. b) A graph showing the summed pixel intensities in the x-direction depicted in FIG. 2a.

FIG. 3

A schematic representation of the image reconstruction method is shown. The detected events or cells are scanned with the laser by moving the stage that is equipped with an encoder. The CCD camera captures the individual sub-images and stores them in computer memory along with the corresponding encoder positions representing the x-y coordinates of the stage. After scanning is complete, the sub-images are combined to form a full reconstructed image of the object by using the encoder values, which are calculated back to the number of pixels that the subsequent sub-images should be shifted with respect to each other. Summation of the shifted sub-images gives the complete reconstructed fluorescent image of the cell.

Figure 4:
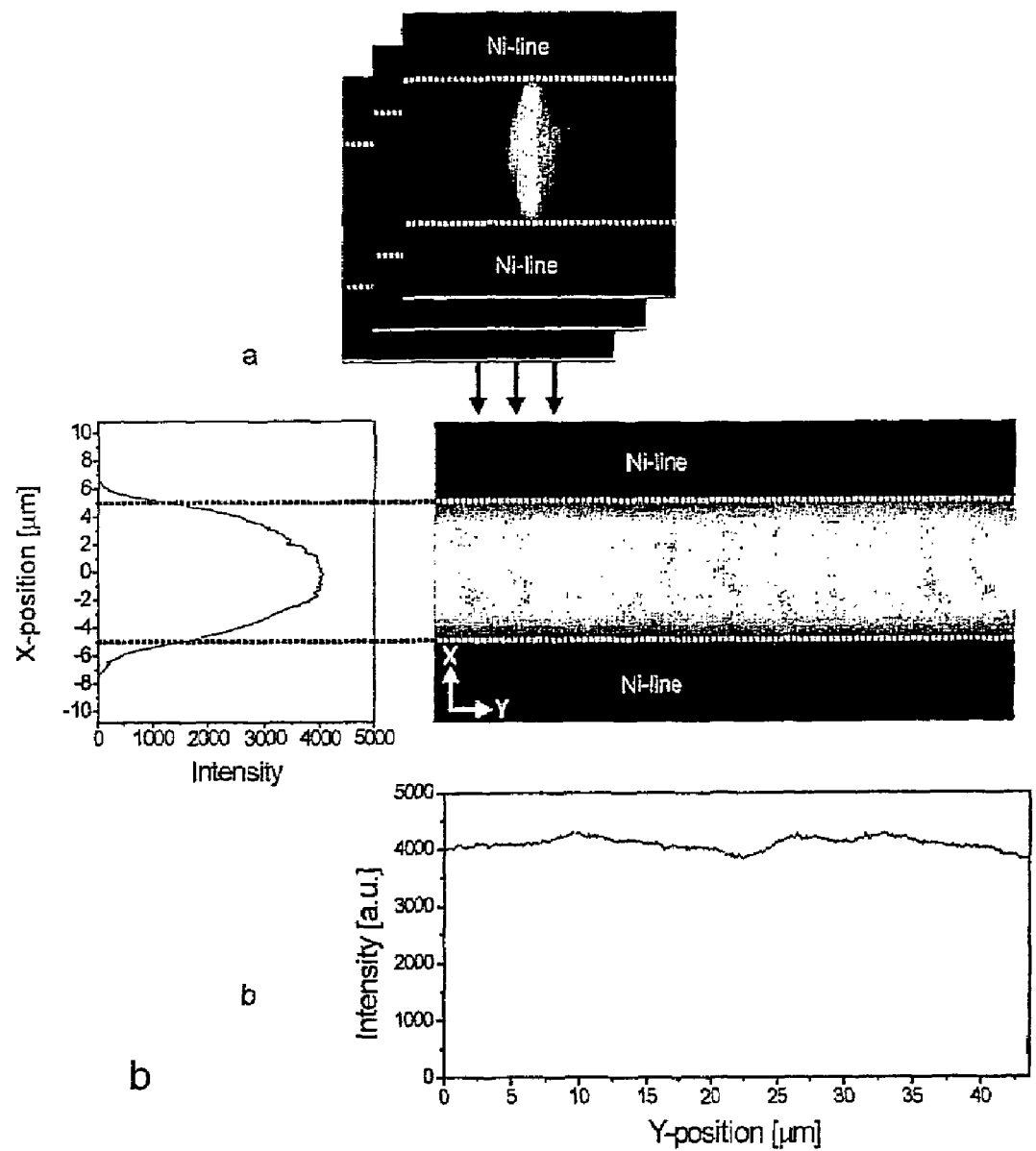

FIG. 4 a) Fluorescent signals captured when a homogeneous layer of dye is scanned. b) Two graphs showing the sums of the fluorescent intensities in the x- and y-directions for the dye scanned in FIG. 4a.

FIG. 5 a) A graphical representation of the solid angle captured by the objective as a function of the position in the chamber. The numerical aperture (NA) of the compact disk (CD) objective in air is 0.45, resulting in an effective NA of 0.34 inside the chamber on the stage. This NA corresponds to a solid angle ($\Omega$) of 0.37 sr. The spacing of the nickel lines is 10 µm. The circle represents an aligned object with a diameter of 7 µm. The effective collecting angle of two points is indicated in the figure. b) The graph shows the relative sum of the calculated solid angles of FIG. 4a in the z-direction.

FIG. 6 a) Scatter plot of CD45 antibody-APC/Cy7 versus CAM5.2 antibody-APC fluorescence of SKBR3 cells spiked into whole blood, captured and aligned by EpCAM antibody-labeled magnetic nanoparticles. Some representative sub-images of the measured events of region 1, the SKBR3 cell region, and of the broad band containing the debris are shown. Region 2 is the region where the leukocytes would appear, if present, and aligned along the Ni lines. b) Full image of an SKBR3 cell with its corresponding measured fluorescence signals.

FIG. 7

Scatter plot of Oxazine 750 fluorescence versus CD4-APC fluorescence of white blood cells in whole blood captured and aligned by CD45-labeled magnetic nanoparticles. Some representative images of the monocyte and granulocyte regions are shown.

FIG. 8

Time resolved imaging of Oxazine 750 stained CD45 ferrofluid captured leukocytes in whole blood utilizing the Cell Tracks system: time span is 0 to 120 sec at 20 sec intervals.

DETAILED DESCRIPTION OF THE INVENTION

The invention will now be further described in reference to preferred embodiments in the following description:

Positional information:

Referring again to FIG. 1, efore a full image of a previous measured event can be made, wherein a full image is defined as a reconstructed image consisting of combined multiple digitized sub-images, the event must be re-located on the sample chamber in FIG. 1, for which spatial information as x-y sample coordinates for each sub-image is needed. To obtain positional information in the y-direction, the stage, which moves both the magnets and sample chamber, has been equipped with an encoder that has a resolution of 0.2 um. The line number for a sub-image of a specific event is measured to give positional information in the x-direction. The encoder signals together with the line number are stored in memory and are coupled to the measured PMT signals for each sub-image. In this manner, all the measured sub-image events have been associated with and indexed to an x-y-position for the sample.

To go back to the position where a specific event or sub-image was measured, the laser focus is shifted by a number of lines equal to the current line number minus the line number on which the specific event was measured. Concurrently, the stage moves in the y-direction to the specific encoder position. An alternative method to obtain encoder signals is to add profiles to the Ni lines described below that provide signals to record the position. This approach further permits the use of a significantly simpler and cheaper stage to move the sample.

Figure 1:
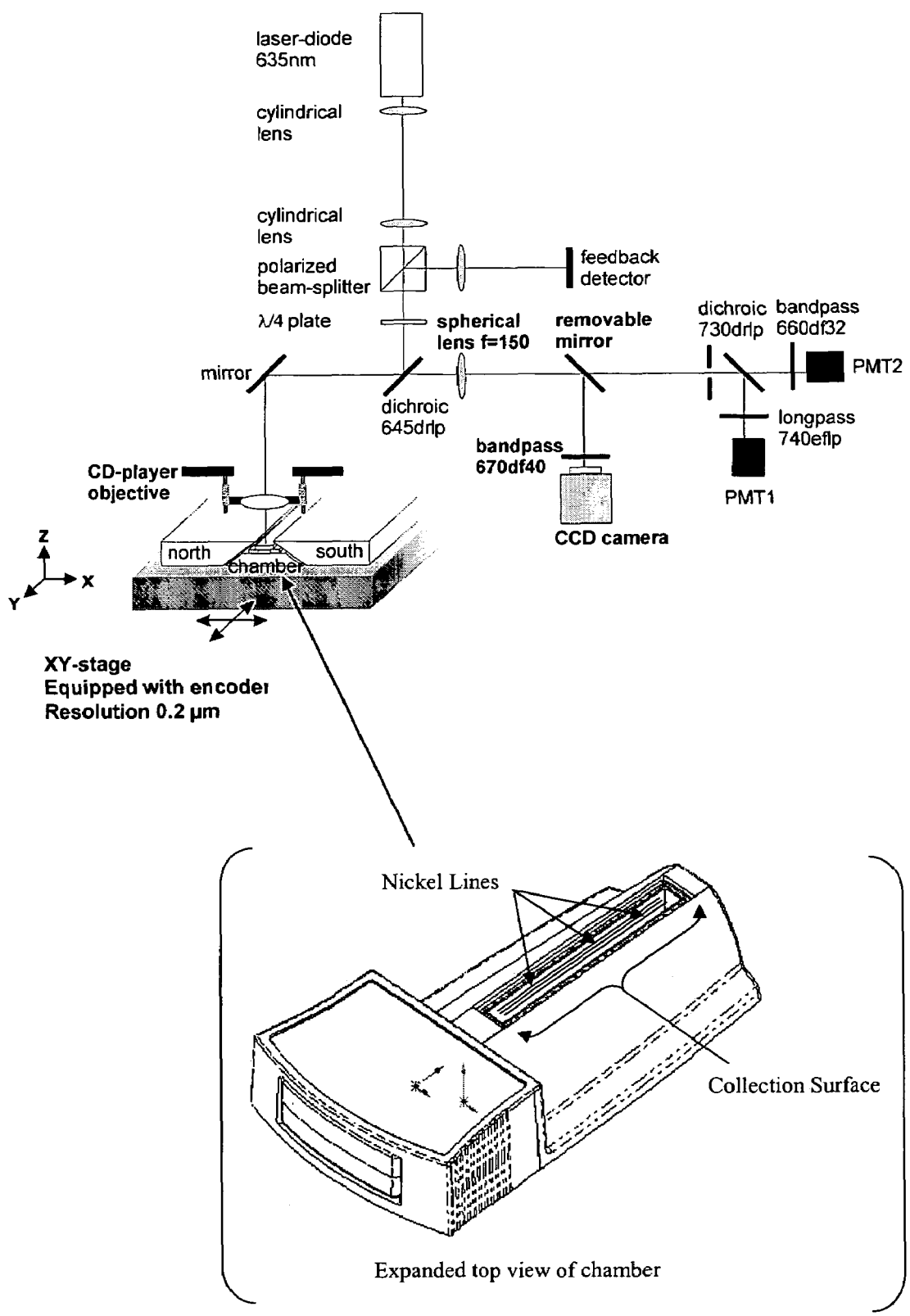
FIG. 1

Method of imaging:

The system shown in FIG. 1 consists of a standard monochrome surveillance charge-coupled device (CCD) camera, frame rate 25 Hz, and with manual gain adjustment. By inserting the removable mirror in to the light beam, the fluorescent light captured by the compact disk (CD) objective is focused by the spherical achromatic lens (f=150 mm) onto the CCD instead of the pinhole. The CD objective consists of a single aspherical lens that has been optimized to obtain a diffraction-limited spot size for a wavelength of 780 nm as used in the CD players. The NA of the lens is 0.45 and the lens diameter is 4 mm. An image of the focal spot, as it is used for scanning the cells, is presented in FIG. 2a. The elliptical shape of the image is obtained with the two cylindrical lenses that are placed at a distance slightly larger than twice their individual focal lengths. The short axis of this elliptical focus is set at 4 μm (FWHM) which is smaller than the diameter of a cell to avoid that more than one cell can be in focus at any one time. The longer axis is larger than the Ni line spacing. The light focused on the Ni lines is reflected and used for feedback control. The Ni lines are present on a 0.5 mm thick glass substrate. Focusing the laser light (635 nm) onto the Ni lines through the glass substrate with the CD-objective, which has not been optimized for this application, results in a non-homogeneous laser focus.

The intensity profile of the laser focus is not only non-homogeneous but, since the diameter of a cell is typically between 5 and 20 μm, it is also smaller than the cell diameter. However, uniform illumination with a laser focus that is smaller than the cell diameter and that has an non-homogeneous intensity profile can be obtained by scanning the laser across the cell surface by moving an optical component in the beam, as is done in the laser scanning microscope (Corle, TR, Confocal Scanning Microscopy and Related Imaging Systems, Academic Press, N.Y., 1995). In the system of the present invention this method would result in a loss of feedback, which in turn would result in a loss of positional information in the x-direction. FIG. 2b shows the intensity profile obtained after adding the individual pixel intensities of the focal spot image of FIG. 2a in the y-direction. The dotted lines indicate a Ni line spacing of 10 μm. The summed intensity profile shows an intensity variation of ±6% across the line spacing. Moving a cell in the y-direction through this focus will have the result that every part of the cell has received an almost equal illumination after it has passed through the laser focus. This method is used to obtain a full high quality fluorescent image of an aligned cell based on summation of individual sub-images.

Figure 3:
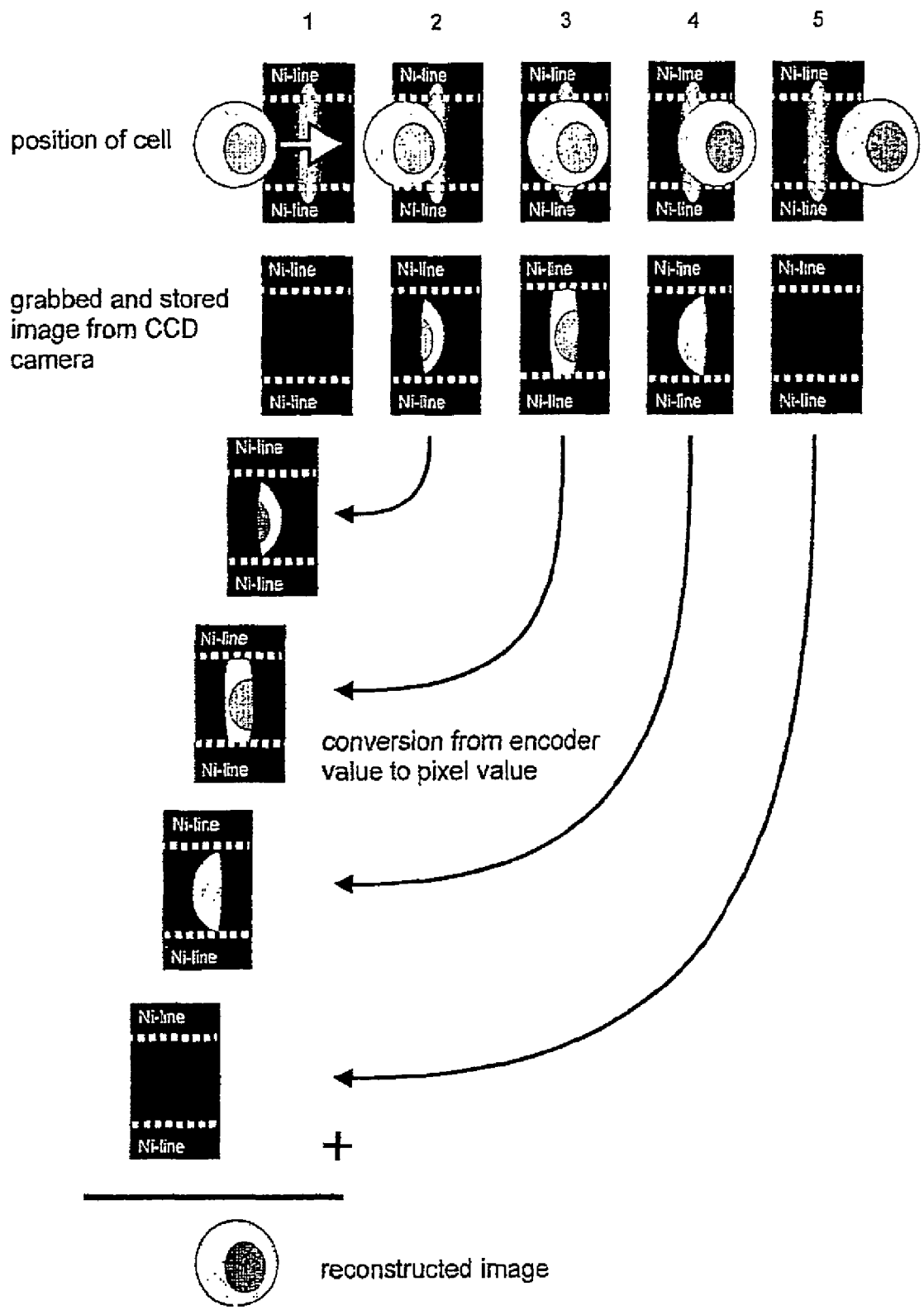

Magnetic stage and chamber:

The magnets and chamber have already been positioned on a stage that moves the cells through the focus in the y-direction. To obtain a full image of a specific cell, the laser focus is shifted to the line where the specific sub-image event was measured and the stage is moved in the y-direction, with a speed of 10 mm/sec, to the corresponding encoder position. The stage is slowed down to a speed of 5 μm/sec when the distance to the cell position is 25 microns. While moving the stage at this low constant speed in the y-direction, the cell is scanned by the laser focus, and the fluorescence signal for each sub-image is captured on the CCD (FIG. 3).

A frame grabber card captures the CCD sub-images at 25 Hz and these are stored in memory. In each subsequent sub-image, a different part of the cell is illuminated since the laser focus in the scan direction is smaller than the cell diameter. Together with the sub-image capture, the encoder position is read and both are stored in computer memory. A total of 40 microns is scanned corresponding to 200 captured sub-images each with 150 times 250 pixels, which are on the average 0.2 μm shifted with respect to each other. This corresponds to a shift of 2.63 pixels on the CCD surface. Using the encoder values the captured sub-images are shifted over a number of pixels corresponding to the difference in their associated encoder values × 2.63, which are then summed or combined. This results in a reconstructed full cell image as is schematically illustrated in FIG. 3. The sub-image resolution in the y-direction is determined by the encoder resolution, which is 0.2 μm. The resolution in the x-direction is determined by the number of pixels in the image recorded in the x-direction and is 0.07 μm per pixel. Both resolutions are smaller than the diffraction limit. Hence, it will be appreciated be those skilled in the art that the ultimate image resolution will not be determined by the encoder or the camera but by the imaging optics.

Figure 5:
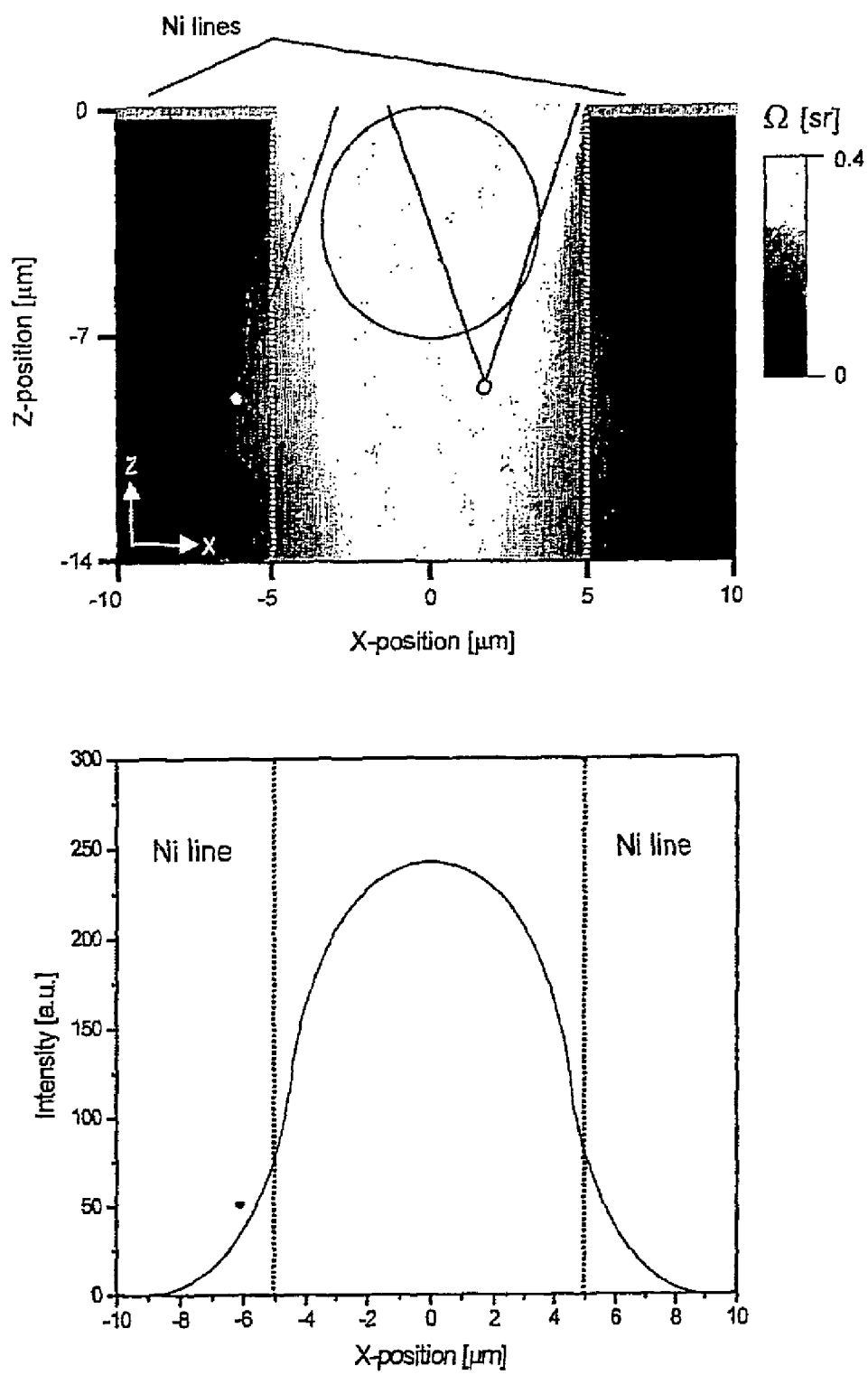

Homogeneity of illumination:

The homogeneity of illumination in the method of this invention was tested with a thin layer of a concentrated fluorescent dye solution that was placed in the plane where the magnetically labeled cells would be aligned between the Ni lines which are spaced 10 μm apart. The dye layer was scanned and imaged at a speed of 5 μm/sec as described above. The sequentially captured sub-images are presented in FIG. 4a. For a uniform layer of fluorescent dye, one would expect a homogeneous fluorescent image, if the illumination were uniform. The obtained image is shown in FIG. 4b. The observed signals, as measured in intensity units along the center trace in the y-direction of the image, were found to vary by ±7%. One explanation for this variation may be non-homogeneity of the dye layer, which would affect the emitted and captured fluorescent light. A second explanation is that the stage did not move with a constant speed. The position of the stage is not synchronized with the frame rate of the camera and the frame grabber card, but images were grabbed at 25 Hz regardless of the speed and position of the stage in the y-direction. If the stage moves faster than 5 μm/sec in a certain region, fewer images would be captured of this region resulting in a lower total intensity. However, the variation in the speed of the stage was measured and turned out to be much smaller than the observed variation in the measured image intensity. The apparent non-uniformity along the center trace must therefore be due the non-homogeneity of the dye layer. The intensity profile in the x-direction or perpendicular to the Ni lines and scan direction is also presented in FIG. 4b. The intensity of the sub-images in this direction have a maximum centered between the Ni lines and fall off near the edges of the Ni lines. The Ni lines obstruct the emitted fluorescent light resulting in a smaller collecting angle, which in turn results in a smaller effective NA of the objective. In FIG. 5a, the effective solid angle detected by the objective is calculated as a function of the position in the chamber. The simulation was performed using a line spacing of 10 μm and a depth or layer thickness of 14 µm. The graph in FIG. 5b shows the sum of the calculated solid angle values of FIG. 5a in the z-direction, thus providing a measure of the collected and measured intensities as a function of the x-position. The observed calculated intensity profile is in agreement with the measured intensities for the uniform dye layer. The effective NA of objects close to the Ni lines is largely reduced resulting in a non-uniform captured intensity in the x-direction even though uniform illumination is used. Objects with a diameter smaller than 7 µm, as is indicated by the circle in FIG. 5a, will be imaged without loss in intensity due to the shielding effect of the Ni lines, since the effective NA in this region is reduced by the Ni lines.

Figure 6:
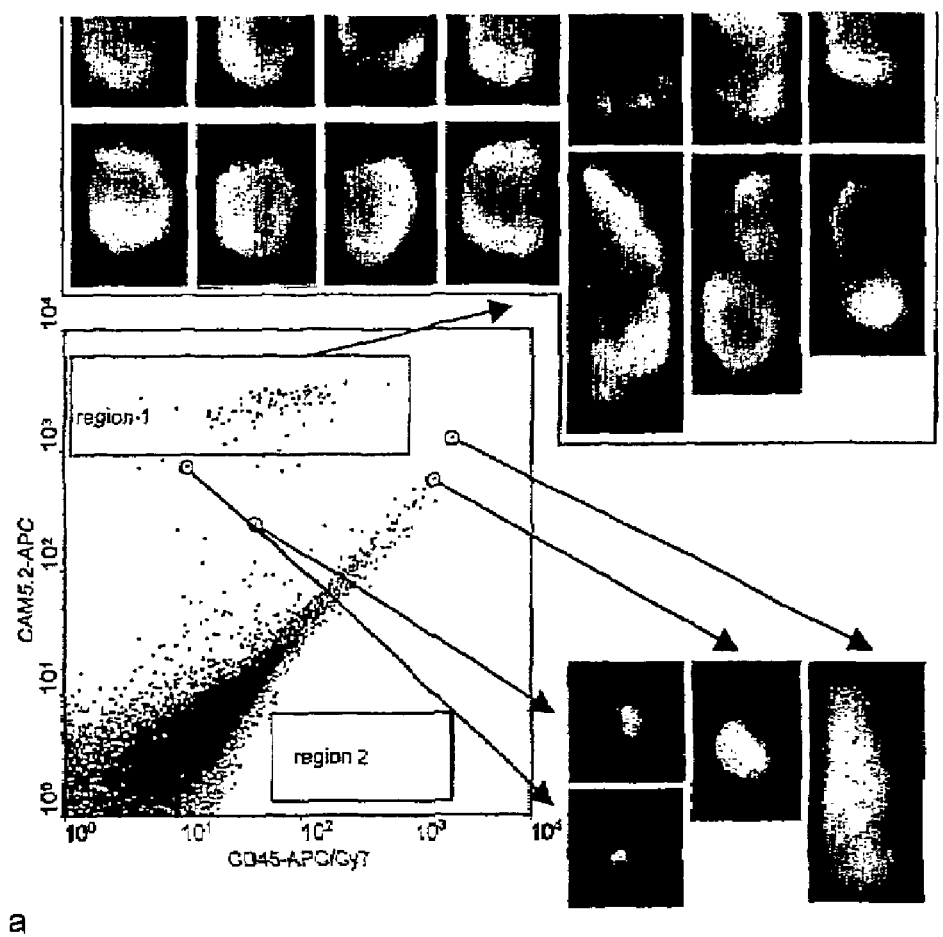
Figure 6:
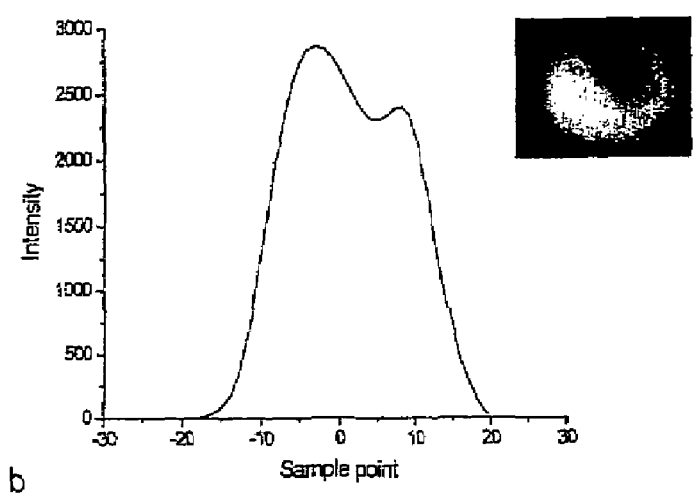

Cell Imaging:

Racila et al. (Proc. Nat. Acad. Sci. 95, 4589-94,1998) described a method for separating breast carcinoma cells from blood using a sequence of steps including immunomagnetic labeling followed by immunophenotyping analysis in a flow cytometer. In the system of this invention, cells can be immunophenotyped and their identity confirmed by providing a fluorescence image. The procedure was tested by the detection of cultured cells of the breast cancer cell line, SKBR3, which were spiked into whole blood. The spiked sample was prepared as described in the Examples. FIG. 6a shows the scatter plot of the APC/Cy7 channel versus the APC channel in flow cytometry. The SKBR3 cells are located in Region 1. Debris appears as the broad band and leukocytes, if present, are located in Region 2. After measuring the scatter plot, some of the events were imaged with the novel imaging technique disclosed herein. After selecting an object or cell in the scatter plot, the imaging system automatically goes back to the measured position of the cell and the imaging routine is started. The set of images taken from events in Region 1 shows cells in which the cytoplasm has been fluorescently stained. The nucleus of these cells is visible as a darker region. The images are different for debris, which is not located in Region 1. FIG. 6b shows an image of an SKBR3 cell with its corresponding measured fluorescence signals. The fluorescent image and measured PMT signals correlate well.

Signal to Noise ratio:

Reducing the imaging scan speed will result in larger number of captured sub-images of a specific event and will, in principle, result in a better signal to noise ratio. However, no improvement in image quality for the APC labeled SKBR3 cells was observed when the image scanning speed was reduced. The limit of the imaging scan velocity is determined by the photo-bleaching rate of the dye molecules. No fluorescence could be detected with the CCD camera if an SKBR3 cell was scanned for the second time, indicating that most of the APC molecules have already been photo-destroyed after the first scan. Reducing the scan speed would, therefore, make no difference in the detected fluorescence signal and would only result in an increase of the fluorescent background. The optimal scan speed is, therefore, dependent on the individual dye characteristics and will be different for each fluorescent dye used. Therefore, to the improve signal to noise ratio it may be better to scan faster. On the other hand scanning faster then 5 µm/sec when using a camera with a frame rate of 25 Hz would result in a loss of resolution since the captured images would be spaced more than 0.2 µm apart. A CCD camera with higher frame rate would be needed to scan faster without losing resolution. Replacing the standard surveillance CCD camera with a more sensitive one would also allow imaging of dimly stained cells.

Confocal Imaging:

The magnetic collection method in the Cell Tracks system does not stress or distort the cells as is commonly observed in cytospin systems using centrifugal deposition on slides. Hence the magnetically aligned cells maintain their native three-dimensional shape and volume. The device and method described herein can also be used to obtain a confocal image of cells and, therefore, to enhance the image quality by allowing a more accurate determination of the 3D-distribution of the fluorescent dye inside the cells (Corle, TR, Confocal Scanning Microscopy and Related Imaging Systems, Academic Press, N.Y., 1995).

Imaging without Ni lines:

In the Cell Tracks system, Ni lines are used to align the cells and to re-locate the cells using the line number on which the cell is measured with its corresponding encoder value. However the imaging invention described herein is not dependent on the presence of Ni lines or magnetic lines and can be used on any surface on which cells or other fluorescent objects of interest are present or can be deposited. Only the encoder data in the scan direction would be needed for reconstructing the image from the stored and grabbed sub-images.

The basic requirements needed for practicing the preferred embodiments of this invention are:

1) The summed intensity profile of the sub-images in the scan direction should be as uniform as possible since this directly relates to the full image quality. In this invention, the variation is less than 6%.

2) The uniformity of the summed intensity profile should extend, in the direction perpendicular to the scan direction, to a range that is wider than the diameter of the object to be scanned.

3) The stage should be able to move with a resolution equal to or smaller than the smallest detail to be observed in a cell.

It will be apparent to those skilled in the art that the improved scanning and imaging systems of the invention is not to be limited by the foregoing descriptions of preferred embodiments, and that the preferred embodiments of the invention which incorporate these improvements, as previously described, have also been found to enable the invention to be employed in many fields and applications to diagnosis of cells and to particulate target species in general. The following Examples illustrate specific embodiments and encompass the currently known best mode of the invention, but are not thereby limited in scope.

EXAMPLE 1

For these experiments, 10 µl of fixed SKBR3 cells (50,000 cells/ml) were mixed with 290 µl of EDTA blood. Also added at the same time were 100 µl of magnetic ferrofluid coated with anti-EpCAM (magnetic particles of about 200 nm size coated with proteins, streptavidin and biotinylated EpCAM antibody), an antibody specific for epithelial cells and known to be present on SKBR3 cells (cultured at Immunicon Corp., Huntingdon Valley, Pa.), 10 µl of allophycocyanin (APC) conjugated to monoclonal antibodies recognizing anti-cytokeratin species or cytoskeletal proteins present in epithelial cells (e.g. SKBR3 cells that are epithelium derived) and 10 µl CD45-APC/Cy7 (Caltag, Burlingame, Calif.) to identify leukocytes and identify leukocytes that may nonspecifically bind to cytokeratin antibody. After 15 minutes' incubation, 50 µl of this blood reaction mixture was injected into the chamber. The chamber was placed in the Cell Tracks magnet assembly and after two minutes' collection time, the feedback system was switched on and the measurements were started. In a single measurement, 40 lines with aligned cells, each 15 mm in length and with a line period of 30 μm were scanned. At a chamber height of 0.5 mm, the scanned volume represents 9 μl. The results of scanning the collected labeled SKBR3 cells with the corresponding measured immuno-fluorescent signals are shown in FIGS. 6a and 6b. FIG. 6a shows a scatter plot of CD45-APC/Cy7 dye versus CAM5.2 antibody-APC fluorescence of SKBR3 cells in whole blood, captured and aligned by EpCAM-labeled magnetic nanoparticles. Some representative images of the measured events of Region 1, the SKBR3 cell region, and of the broad band containing the debris are shown. Region 2 is the region where the leukocytes would appear, if present and aligned along the Ni lines. FIG. 6b shows an image of one SKBR3 cell with its corresponding measured fluorescence signals.

EXAMPLE 2

Figure 7:
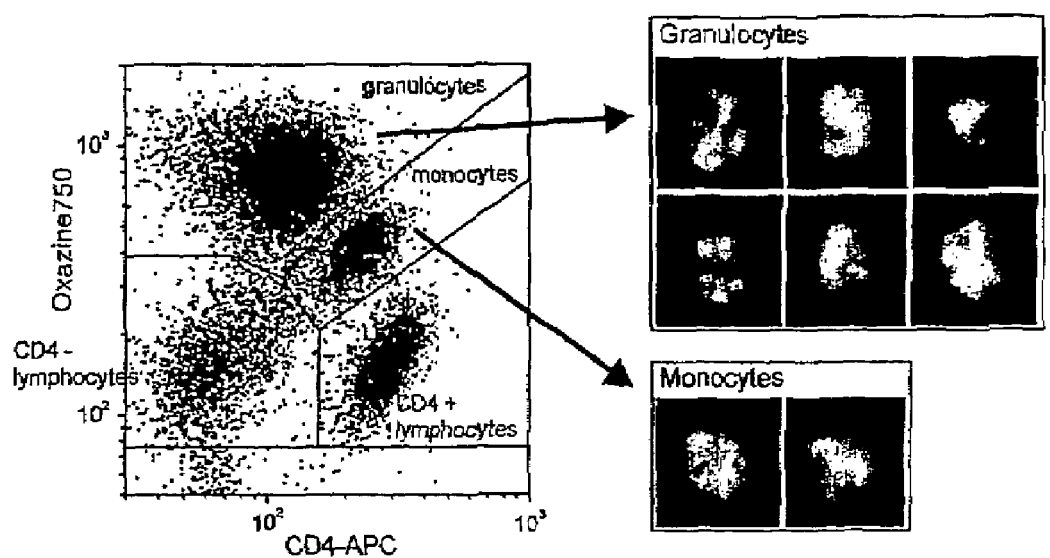

In this experiment 100 μl of EDTA anti-coagulated blood, 50 μl of ferrofluid containing 5 μg of CD45-labeled ferromagnetic nanoparticles, 1.5 μl CD4-APC and 25 μl of $10^{-5}$ M Oxazine 750 perchlorate (Exciton Inc., Dayton, Ohio) were added. The optimum concentration of the reagents was obtained by serial titration of each of the reagents. After incubation for 15 minutes, 300 μl PBS was added and 50 μl of the blood mixture was placed into the capillary that was already placed between the magnets. The capillary has a glass bottom shaped in a way that it fits between the 70° tilted faces of the magnets. Two strips of double-sided tape with a thickness of 0.5 mm (3M Co., St. Paul, Minn.) were placed on the glass with spacing of 3 mm to form the sidewalls of the capillary. Ni lines, about 30 μm wide and about 0.2 μm thick, were produced by standard photolithographic techniques on a 7740 Pyrex® glass wafer (Corning International, Germany). Wafers were cut in pieces of 4 mm × 25 mm and these were placed, with the Ni lines facing the bottom, on the double sided tape to form the top of the capillary. The inner dimensions of the capillary are height=0.5 mm, length=25 mm, width=3 mm. In the measurement presented here the scan speed in the y-direction was 4 mm/sec, the chamber was scanned over 15 mm and 40 lines were scanned, resulting in a measuring time of two and a half minutes. Since the period of the lines is 30 μm, the surface scanned is 18 $mm^2$. As the height of the chamber was 0.5 mm, the scanned volume is 9 μl. For the differential white blood cell count, the addition of reagents resulted in a dilution factor of 4.77. To shorten the time that the cells need to align between lines and to assure that even the weakly magnetic labeled cells would be attracted to the upper surface, the capillary together with the magnets was placed upside down after the blood was placed into the capillary. After two minutes the capillary with the magnets was inverted again and, after approximately one minute, the feedback system was switched on and the measurement was started. To separate the emission spectra, a 660df32 bandpass filter for the APC fluorescence and a 730df100 bandpass filter (both filters from Omega Optical Co., Brattleboro, Vt.) for the Oxazine 750 were used. As the fluorescence intensity of Oxazine 750 stained cells is significantly greater than that of immuno-fluorescent CD4-APC labeled cells, compensation of the spectral overlap is required. A typical example of the scatter plot obtained after compensation is shown in FIG. 7. Four populations are clearly visible and were identified as CD4+ lymphocytes, CD4+ monocytes, CD4− lymphocytes and neutrophilic granulocytes. The gate settings illustrated in the figure were used to determine the number of events in each gate. Total number of leukocytes measured was 12,350 and the measuring time was 2.5 minutes. To examine the distribution of the fluorescence from the detected objects, software was written to allow the user to point at the object of interest in the scatter plot. The system then moved to the location of this event and an image was taken. Surprisingly, the images clearly demonstrated that the fluorescence obtained from the Oxazine 750 staining was not derived from the nucleus but from the granules (Shapiro H M, Stephens S: Flow cytometry of DNA Content Using Oxazine 750 or Related Laser Dyes With 633 nm Excitation. Cytometry 1986; 7: 107-110). Six images obtained from the events in the granulocyte gate and two images from events in the monocyte gate are shown.

EXAMPLE 3

Figure 8:
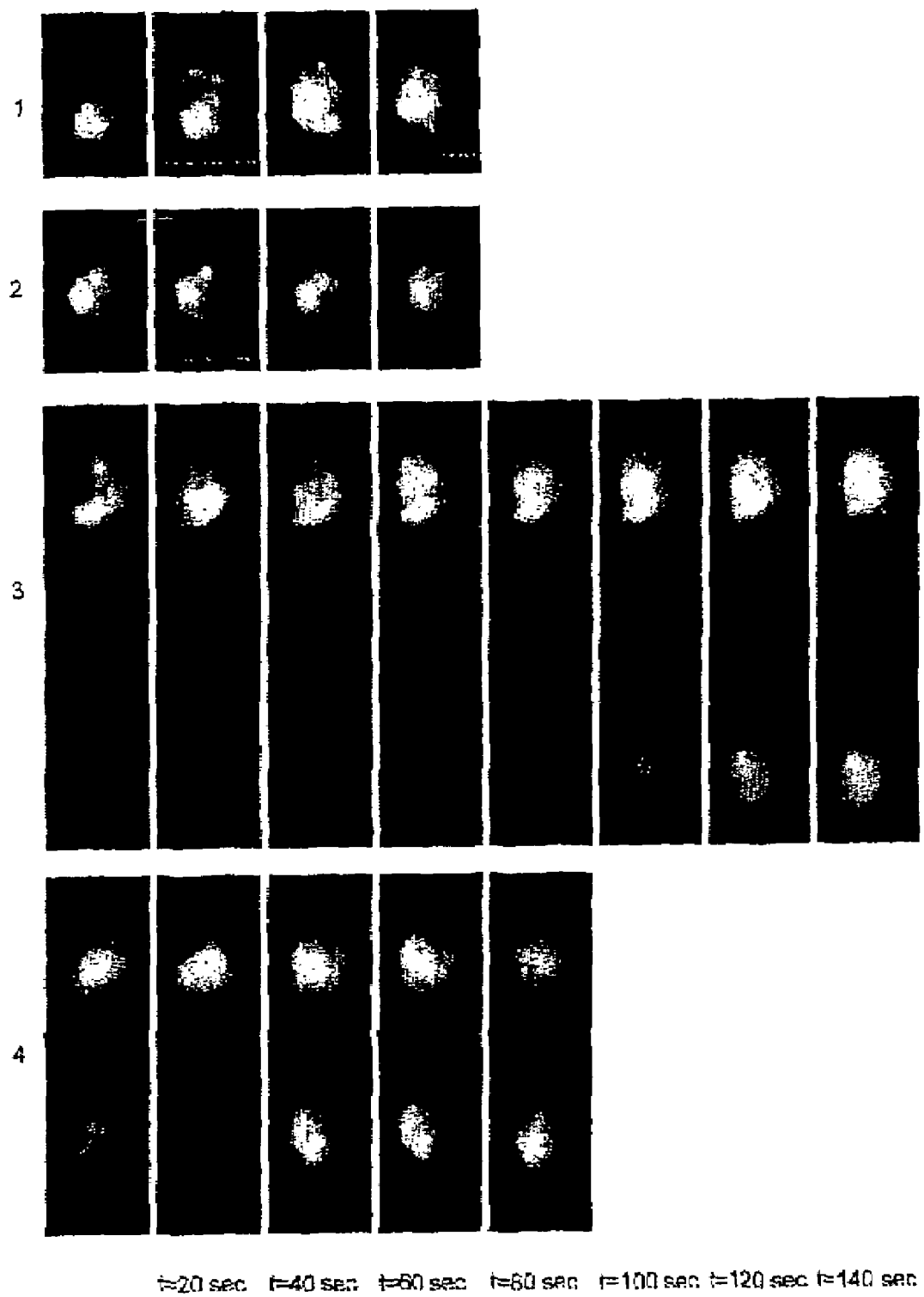

The experiment described in example 2 was repeated but time resolved images were taken with the Cell Tracks system from Oxazine 750 stained and CD45 ferrofluid captured leukocytes in whole blood. FIG. 8 shows four examples of images taken at 20 seconds intervals. The distribution of the fluorescence within the cells is clearly changing between the time intervals and different cells behave differently as is obvious from the cells followed in frame 3 and 4. In both frames images from two cells in close proximity are taken and the differences in uptake and cellular distribution of the Oxazine 750 are apparent. From these examples it is obvious that the Cell Track system has a unique capability to perform functional analysis of cells as, for example, one can study the responses of cells in blood to drugs or other components in real time.

Although the present invention has been described with reference to specific embodiments, workers skilled in the art will recognize that many variations may be made therefrom, for example in the particular experimental conditions herein described, and it is to be understood and appreciated that the disclosures in accordance with the invention show only some preferred embodiments and objects and advantages of the invention without departing from the broader scope and spirit of the invention. It is to be understood and appreciated that these discoveries in accordance with this invention are only those which are illustrative of the many additional potential applications of the apparatus and methods that may be envisioned by one of ordinary skill in the art, and thus are not in any way intended to be limiting of the invention. Accordingly, other objects and advantages of the invention will be apparent to those skilled in the art from the following detailed description, together with the appended claims.

What is claimed is:

1. An apparatus for automatically scanning magnetically and detectably labeled micron-sized objects on a planar surface whereon said objects are aligned in a linear array by magnetic means, comprising:
    a. one or more laser light sources;
    b. a polarized beam splitter with feedback detector;
    c. a dichroic mirror assembly;
    d. a focusing lens assembly;
    e. a sample chamber having affixed thereto at least two parallel nickel lines in the x-direction thereby to form a linear array, said sample chamber being inserted into a magnet system stably affixed to said x-y stage, thereby providing means for collecting, aligning and transporting said collected labeled objects into said focused light beam in a stepwise and digitized mode;

f. means for acquiring the sequential digitized signals images emanating from said labeled objects as digitized sub-images by means of a CCD camera and one or more PMT tubes;

g. means for storing said acquired sub-images in computer memory indexed to the corresponding z-y stage position; and h. means for reconstructing a full image having combined multiple digitized sub-images of said objects on said linear array.

2. The apparatus of claim 1 wherein the parallel nickel lines on said linear array are spaced about 10 um apart.

3. The apparatus of claim 1 in which the CCD camera has a frame rate commensurate with the scan speed of the stage, thereby to maintain a resolution of at least 0.2 um.

4. An apparatus for analytical imaging of target entities, said apparatus comprising:

a. a sample chamber which includes a collection surface wherein said collection surface comprises nickel lines on a glass substrate;

b. an arrangement of magnets capable of manipulating magnetically labeled target entities towards said collection surface;

c. at least one light source;

d. a camera capable of capturing sub-images of said collected target entities; and e. a computer capable of re-combining said sub-images to construct a complete image of said collected target entities.

5. The apparatus of claim 4, in which said light source is a laser.

* * * * *